United States Patent

Hofer et al.

[11] 4,345,078
[45] Aug. 17, 1982

[54] COMBATING ARTHROPODS WITH O-ALKYL-O-[5-CARBALKOXY-7-ALKYL-PYRAZOLO(1,5-α)-PYRIMIDIN-2-YL]-(THIONO) (THIOL)-PHOSPHORIC (PHOSPHONIC) ACID ESTERS

[75] Inventors: Wolfgang Hofer; Fritz Maurer; Hans-Jochem Riebel, all of Wuppertal; Rolf Schröder, Velbert; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 836,339

[22] Filed: Sep. 26, 1977

[30] Foreign Application Priority Data

Oct. 2, 1976 [DE] Fed. Rep. of Germany ....... 2644642

[51] Int. Cl.³ ..................... C07D 487/04; A01N 9/22
[52] U.S. Cl. .................... 544/244; 424/251; 544/281; 71/86
[58] Field of Search .............. 260/256.4 E, 256.5 R; 424/251; 544/244

[56] References Cited

U.S. PATENT DOCUMENTS 3,402,176  9/1968  Schicke ............... 544/244
3,478,029 11/1969  Schicke ............... 544/244
3,496,178  2/1970  Scherer et al. ....... 544/244
3,950,337  4/1976  Hoffmann et al. ..... 544/244

FOREIGN PATENT DOCUMENTS 676802  2/1966  Belgium .
2241395 2/1974  Fed. Rep. of Germany .

Primary Examiner—Donald G. Daus
Assistant Examiner—James H. Turnipseed
Attorney, Agent, or Firm—Sprung, Horn, Kramer & Woods

[57] ABSTRACT

O-Alkyl-O-[5-carbalkoxy-7-alkyl-pyrazolo-(1,5-α)-pyrimidin-2-yl]-(thiono) (thiol)-phosphoric (phosphonic) acid esters of the formula

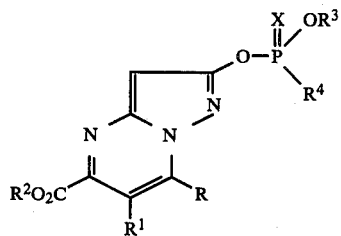

in which
R, $R^2$ and $R^3$ each independently is alkyl,
$R^1$ is hydrogen or alkyl,
$R^4$ is alkoxy, alkylthio, alkyl or phenyl, and
X is oxygen or sulphur which possess arthropodicidal properties.

1 Claim, No Drawings

COMBATING ARTHROPODS WITH O-ALKYL-O-[5-CARBALKOXY-7-ALKYL-PYRAZOLO(1,5-α)-PYRIMIDIN-2-YL]-(THIONO)(THIOL)-PHOSPHORIC (PHOSPHONIC) ACID ESTERS

The present invention relate to and has for its objects the provision of particular new O-alkyl-O-[5-carbalkoxy-7-alkyl-pyrazolo(1,5-α)-pyrimidin-2-yl](thiono)(thiol)-phosphoric(phosphonic) acid esters which possess arthropodicidal properties, active compositions in the form of mixtures of such compounds with solid and liquid dispersible carrier vehicles, and methods for producing such compounds and for using such compounds in a new way especially for combating pests, e.g. arthropods with other and further objects becoming apparent from a study of the within specification and accompanying examples.

It is already known that certain pyrazolopyrimidinylthiono-phosphoric acid esters, for example, O,O-diethyl-O-[5,7-dimethyl- and 6-chloro-5,7-dimethyl-pyrazolo(1,5-α)-pyrimidin-2-yl]-thionophosphoric acid esters, exhibit a pesticidal, especially insecticidal and acaricidal, action (see Belgian Pat. No. 676,802 and U.S. Pat. No. 3,950,337).

The present invention now provides, as new compounds, the pyrazolopyrimidinyl-(thiono)(thiol)-phosphoric(phosphonic) acid esters of the general formula

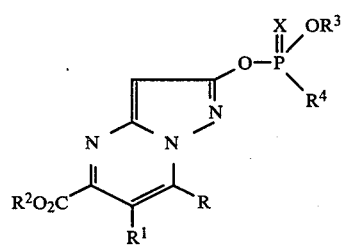

in which
R, $R^2$ and $R^3$, which need not be identical, each represent alkyl,
$R^1$ represents hydrogen or alkyl,
$R^4$ represents alkoxy, alkylthio, alkyl or phenyl, and
X represents oxygen or sulphur.

Preferably, R, $R^2$ and $R^3$, which need not be identical, each represent straight-chain or branched alkyl with 1 to 7 (especially 1 to 5) carbon atoms, $R^1$ represents hydrogen, methyl or ethyl, $R^4$ represents straight-chain or branched alkoxy or alkylthio with 1 to 6 (especially 1 to 4) carbon atoms, straight-chain or branched alkyl with 1 to 5 (especially 1 to 3) carbon atoms or phenyl and X represents sulphur.

Surprisingly, the pyrazolopyrimidinyl(thiono)(thiol)-phosphoric(phosphoric) acid esters according to the invention exhibit a substantially greater insecticidal and acaricidal action than the previously known pyrazolopyrimidinylthionophosphoric acid esters of analogous structure and of the same type of action. The compounds according to the invention thus represent a genuine enrichment of the art.

The invention also provides a process for the preparation of a pyrazolopyrimidinyl(thiono)(thiol)-phosphoric(phosphonic) acid ester of the formula (I), in which a (thiono)(thiol)phosphoric(phosphonic) acid ester halide of the general formula

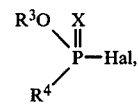

in which
$R^3$, $R^4$ and X have the above-mentioned meanings, and
Hal represents halogen, preferably chlorine,
is reacted, if appropriate in the presence of a diluent or solvent, with a 2-hydroxypyrazolopyrimidine of the general formula

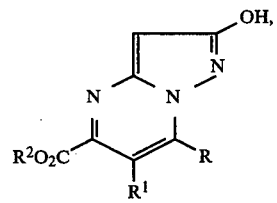

in which
R, $R^1$ and $R^2$ have the above-mentioned meanings, the latter being employed as such, in the presence of an acid acceptor, or in the form of an alkali metal salt, alkaline earth metal salt or ammonium salt.

If O-ethylthionophenylphosphonic acid ester chloride and 5-carbisopropoxy-2-hydroxy-7-methyl-pyrazolo(1,5-α)-pyrimidine are used as starting materials, the course of the reaction can be represented by the following equation:

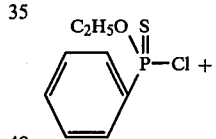

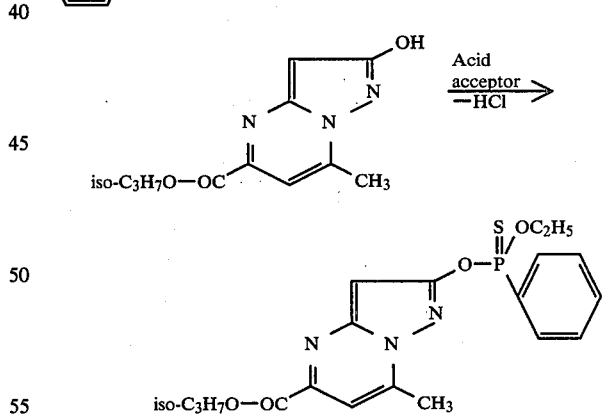

The (thiono)(thiol)phosphoric(phosponic) acid ester halides (II) to be used as starting material are known and can easily be prepared in accordance with customary processes.

The following may be mentioned as individual examples: O,O-dimethyl-, O,O-diethyl-, O,O-di-n-propyl-, O,O-di-isopropyl, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-isopropyl-O-butyl(thiono)-phosphoric acid diester chloride; O,S-dimethyl-, O,S-diethyl-, O,S-di-n-propyl-, O,S-di-iso-propyl-, O,S-di-n-butyl-, O,S-di-iso-butyl-, O,S-di-sec.-butyl-, O,S-di-n-pentyl-, O-ethyl-S-n-propyl-, O-ethyl-S-iso-propyl-, O-ethyl-S-n-butyl, O-ethyl-S-sec.-butyl-, O-n-propyl-S-ethyl-, O-n-propyl-S-iso-propyl-, O-n-butyl-S-n-propyl- and O-sec.-butyl-S-ethyl-(thiono)-thiolphosphoric acid diester chloride; and O-methyl-, O-ethyl-, O-n-propyl-, O-iso-propyl-, O-n-butyl-, O-iso-butyl-, O-sec.-butyl-, O-tert.-butyl- and O-n-pentyl-methane-, -ethane-, -n-propane-, -iso-propane-, -n-butane-, -iso-butane-, -sec.-butane- and phenyl-(thiono)-phosphonic acid ester chloride.

The 2-hydroxypyrazolopyrimidines (III) also to be used as starting materials can be prepared in accordance with processes known from the literature by, for example, reacting 3-amino-5-pyrazolone with acylpyruvic acid alkyl esters in the presence of gaseous hydrochloric acid.

The following may be mentioned as individual examples: 5-carbomethoxy-7-methyl-, 5-carbethoxy-7-methyl-, 5-carbo-n-propoxy-7-methyl-, 5-carb-iso-propoxy-7-methyl-, 5-carbo-n-butoxy-7-methyl-, 5-carb-iso-butoxy-7-methyl-, 5-carbo-sec.-butoxy-7-methyl-, 5-carbomethoxy-7-ethyl-, 5-carbethoxy-7-ethyl-, 5-carbo-n-propoxy-7-ethyl-, 5-carb-iso-propoxy-7-ethyl-, 5-carbo-n-butoxy-7-ethyl-, 5-carb-iso-butoxy-7-ethyl-, 5-carbo-sec.-butoxy-7-ethyl-, 5-carbomethoxy-7-n-propyl-, 5-carbethoxy-7-n-propyl-, 5-carbo-n-propoxy-7-n-propyl-, 5-carb-iso-propoxy-7-n-propyl-, 5-carbo-n-butoxy-7-n-propyl-, 5-carb-iso-butoxy-7-n-propyl-, 5-carbo-sec.-butoxy-7-n-propyl-, 5-carbomethoxy-7-iso-propyl-, 5-carbethoxy-7-iso-propyl-, 5-carbo-n-propoxy-7-iso-propyl-, 5-carb-iso-propoxy-7-iso-propyl-, 5-carbo-n-butoxy-7-iso-propyl-, 5-carb-iso-butoxy-7-iso-propyl-, 5-carbo-sec.-butoxy-7-iso-propyl-, 5-carbomethoxy-7-n-butyl-, 5-carb-ethoxy-7-n-butyl-, 5-carbo-n-propoxy-7-n-butyl-, 5-carb-iso-propoxy-7-n-butyl-, 5-carbo-n-butoxy-7-n-butyl-, 5-carb-iso-butoxy-7-n-butyl-, 5-carbo-sec.-butoxy-7-n-butyl-, 5-carbomethoxy-7-iso-butyl-, 5-carbethoxy-7-iso-butyl-, 5-carbo-n-propoxy-7-iso-butyl-, 5-carb-iso-propoxy-7-iso-butyl-, 5-carbo-n-butoxy-7-iso-butyl-, 5-carb-iso-butoxy-7-iso-butyl-, 5-carbo-sec.-butoxy-7-iso-butyl-, 5-carbo-methoxy-7-sec.-butyl-, 5-carbethoxy-7-sec.-butyl-, 5-carbo-n-propoxy-7-sec.-butyl-, 5-carb-iso-propoxy-7-sec.-butyl-, 5-carbo-n-butoxy-7-sec.-butyl-, 5-carb-iso-butoxy-7-sec.-butyl-, 5-carbo-sec.-butoxy-7-sec.-butyl-, 5-carbomethoxy-7-tert.-butyl-, 5-carbethoxy-7-tert.-butyl-, 5-carbo-n-propoxy-7-tert.-butyl-, 5-carb-iso-propoxy-7-tert.-butyl-, 5-carbo-n-butoxy-7-tert.-butyl-, 5-carb-iso-butoxy-7-tert.-butyl-, 5-carbo-sec.-butoxy-7-tert.-butyl-, 5-carbomethoxy-7-n-pentyl-, 5-carbethoxy-7-n-pentyl-, 5-carbo-n-propoxy-7-n-pentyl-, 5-carb-iso-propoxy-7-n-pentyl-, 5-carbo-n-butoxy-7-n-pentyl-, 5-carb-iso-butoxy-7-n-pentyl., 5-carbo-sec.-butoxy-7-n-pentyl-, 5-carbomethoxy-6,7-dimethyl-, 5-carbethoxy-6,7-dimethyl-, 5-carbo-n-propoxy-6,7-dimethyl-, 5-carb-iso-propoxy-6,7-dimethyl-, 5-carbo-n-butoxy-6,7-dimethyl-, 5-carb-iso-butoxy-6,7-dimethyl-, 5-carbo-sec.-butoxy-6,7-dimethyl-, 5-carbomethoxy-6-methyl-7-ethyl-, 5-carbethoxy-6-methyl-7-ethyl-, 5-carbo-n-propoxy-6-methyl-7-ethyl-, 5-carb-iso-propoxy-6-methyl-7-ethyl-, 5-carbo-n-butoxy-6-methyl-7-ethyl-, 5-carb-iso-butoxy-6-methyl-7-ethyl-, 5-carbo-sec.-butoxy-6-methyl-7-ethyl-, 5-carbo-methoxy-6-methyl-7-n-propyl-, 5-carbethoxy-6-methyl-7-n-propyl-, 5-carbo-n-propoxy-6-methyl-7-n-propyl-, 5-carbo-iso-propoxy-6-methyl-7-isopropyl-, 5-carbo-n-butoxy-6-methyl-7-n-propyl-, 5-carb-iso-butoxy-6-methyl-7-n-propyl-, 5-carbo-sec.-butoxy-6-methyl-7-n-propyl-, 5-carbo-methoxy-6-methyl-7-iso-propyl-, 5-carbethoxy-6-methyl-7-iso-propyl-, 5-carbo-n-propoxy-6-methyl-7-iso-propyl-, 5-carb-iso-propoxy-6-methyl-7-iso-propyl-, 5-carbo-n-butoxy-6-methyl-7-iso-propyl-, 5-carb-iso-butoxy-6-methyl-7-iso-propyl-, 5-carbo-sec.-butoxy-6-methyl-7-iso-propyl-, 5-carbomethoxy-6-methyl-7-n-butyl-, 5-carbethoxy-6-methyl-7-n-butyl-, 5-carbo-n-propoxy-6-methyl-7-n-butyl-, 5-carb-iso-propoxy-6-methyl-7-n-butyl-, 5-carbo-n-butoxy-6-methyl-7-n-butyl-, 5-carb-iso-butoxy-6-methyl-7-n-butyl-, 5-carbo-sec.-butoxy-6-methyl-7-n-butyl-, 5-carbomethoxy-6-methyl-7-iso-butyl-, 5-carbethoxy-6-methyl-7-iso-butyl-, 5-carbo-n-propoxy-6-methyl-7-iso-butyl-, 5-carb-iso-propoxy-6-methyl-7-iso-butyl-, 5-carbo-n-butoxy-6-methyl-7-iso-butyl-, 5-carb-iso-butoxy-6-methyl-7-iso-butyl-, 5-carbo-sec.-butoxy-6-methyl-7-iso-butyl-, 5-carbomethoxy-6-methyl-7-sec.-butyl-, 5-carbethoxy-6-methyl-7-sec.-butyl, 5-carbo-n-propoxy-6-methyl-7-sec.-butyl-, 5-carb-iso-propoxy-6-methyl-7-sec.-butyl-, 5-carbo-n-butoxy-6-methyl-7-sec.-butyl-, 5-carb-iso-butoxy-6-methyl-7-sec.-butyl-, 5-carbo-sec.-butoxy-6-methyl-7-sec.-butyl-, 5-carbomethoxy-6-methyl-7-tert.-butyl-, 5-carbethoxy-6-methyl-7-tert.-butyl-, 5-carbo-n-propoxy-6-methyl-7-tert.-butyl-, 5-carb-iso-propoxy-6-methyl-7-tert.-butyl-, 5-carbo-n-butoxy-6-methyl-7-tert.-butyl-, 5-carb-iso-butoxy-6-methyl-7-tert.-butyl-, 5-carbo-sec.-butoxy-6-methyl-7-tert.-butyl-, 5-carbomethoxy-6-methyl-7-n-pentyl-, 5-carbethoxy-6-methyl-7-n-pentyl-, 5-carbo-n-propoxy-6-methyl-7-n-pentyl-, 5-carb-iso-propoxy-6-methyl-7-n-pentyl-, 5-carbo-n-butoxy-6-methyl-7-n-pentyl-, 5-carb-iso-butoxy-6-methyl-7-n-pentyl-, 5-carbo-sec.-butoxy-6-methyl-7-n-pentyl-, 5-carbomethoxy-6,7-diethyl-, 5-carbethoxy-6,7-diethyl-, 5-carbo-n-propoxy-6,7-diethyl-, 5-carb-iso-propoxy-6,7-diethyl-, 5-carbo-n-butoxy-6,7-diethyl-, 5-carb-iso-butoxy-6,7-diethyl-, 5-carbo-sec.-butoxy-6,7-diethyl-, 5-carbomethoxy-6-ethyl-7-n-propyl-, 5-carbethoxy-6-ethyl-7-n-propyl-, 5-carbo-n-propoxy-6-ethyl-7-n-propyl-, 5-carb-iso-propoxy-6-ethyl-7-n-propyl-, 5-carbo-n-butoxy-6-ethyl-7-n-propyl-, 5-carb-iso-butoxy-6-ethyl-7-n-propyl- and 5-carbo-sec.-butoxy-6-ethyl-7-n-propyl-2-hydroxypyrazolo(1,5-α)-pyrimidine.

The process for the preparation of the compounds according to the invention is preferably carried out in the presence of a suitable solvent or diluent. Virtually all organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 100° C., preferably at from 10° to 40° C.

In general, the reaction is allowed to take place under normal pressure.

To carry out the process, the starting materials are in most cases employed in stoichiometric amounts. An excess of one or the other reactant produces no significant advantages. The reactants are preferably combined in one of the above-mentioned solvents and stirred for one or more hours at room temperature to complete the reaction. The batch is then poured into ice-water and is extracted by shaking with an organic solvent, for example toluene. The organic phase is then worked up in the usual manner by washing, drying and distilling off the solvent.

The new compounds are in most cases obtained in the form of oils, which frequently cannot be distilled without decomposition, but are freed from the last volatile constituents by so-called "slight distillation", that is to say by prolonged heating under reduced pressure to moderately elevated temperatures, and are purified in this manner. They are characterized by the refractive index. Some of the compounds are obtained in a crystalline form and are characterized by their melting point.

As already mentioned, the compounds according to the present invention are distinguished by an excellent insecticidal or acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculate;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata, lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., Li Meligethes aeneus, Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelyra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus galli-* nae, *Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin, hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides or nematicides, fungicides, bactericides, rodenticides, herbicides, fertilizers growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplate overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples.

The process of the present invention is illustrated by the following preparative examples:

EXAMPLE 1

(a) The required starting materials (III) could be prepared, for example, as described below:

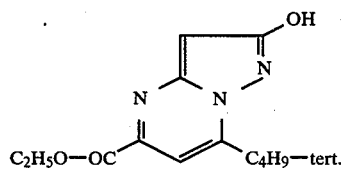

Gaseous hydrochloric acid was passed into a mixture of 40 g (0.1 mol) of pivaloylpyruvic acid ethyl ester, 19.8 g (0.2 mol) of 3-amino-5-pyrazolone and 200 ml of ethanol in such a way that the reaction temperature did not exceed 40° C. When the exothermic reaction had subsided, the introduction of the hydrochloric acid was discontinued and the reaction mixture was stirred for a further 2 hours at 20° C. 400 ml of water were then added and the pH was brought to about 3–4 by adding sodium hydroxide solution. The product which had crystallized out was filtered off and dried. 37 g (72% of theory) of 5-carbethoxy-7-tert.-butyl-2-hydroxypyrazolo(1,5-α)-pyrimidine were obtained in the form of yellow crystals of melting point 201° C.

The following compounds of the formula

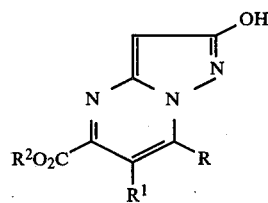

could be prepared analogously:

TABLE 1

| R | $R^1$ | $R^2$ | Yield (% of theory) | Melting point °C. |
|---|---|---|---|---|
| $C_4H_9$—tert. | H | $C_3H_7$—iso | 74 | 184–185 |
| $C_4H_9$—tert. | H | $CH_3$ | 81 | 191–194 |
| $C_2H_5$ | $CH_3$ | $C_2H_5$ | 32 | 163 |
| $C_3H_7$—iso | H | $C_3H_7$—iso | 73 | 150 |

(b)

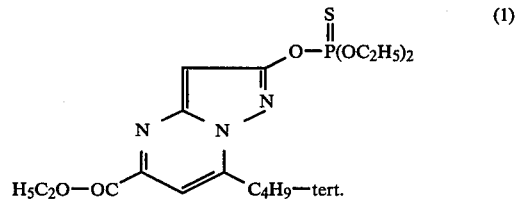

18.8 g (0.1 mol) of O,O-diethylthionophosphoric acid diester chloride were added dropwise at 20° C. to a suspension of 26.3 g (0.1 mol) of 5-carbethoxy-7-tert.-butyl-2-hydroxypyrazolo(1,5-α)-pyrimidine, 14.5 g (0.105 mol) of potassium carbonate and 200 ml of dimethylformamide. The reaction mixture was stirred for a further 3 hours at 20° C. and was then poured into 500 ml of ice water. The batch was extracted twice with 100 ml of toluene at a time. The combined toluene extracts were washed with water, dried over sodium sulphate and then concentrated. After slight distillation, 21 g (52% of theory) of O,O-diethyl-O-[5-carbethoxy-7-tert.-butyl-pyrazolo(1,5-α)-pyrimidin-2-yl]thionophosphoric acid ester were obtained in the form of a yellow oil having a refractive index $n_D^{20}$ of 1.5401.

The following compounds of the formula

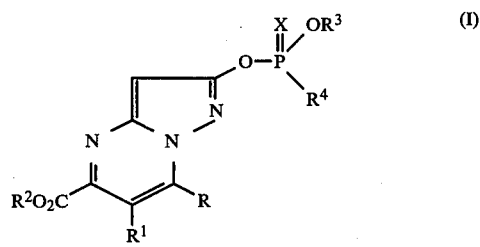

could be prepared analogously:

TABLE 2

| Compound No. | R | $R^1$ | $R^2$ | $R^3$ | $R^4$ | X | Yield (% of theory) | Physical data (refractive index; melting point [°C.]) |
|---|---|---|---|---|---|---|---|---|
| 2 | $C_4H_9$—tert. | H | $C_3H_7$—iso | $C_2H_5$ | $OC_3H_7$—n | S | 66 | $n_D^{20}$:1.5357 |
| 3 | $C_4H_9$—tert. | H | $C_3H_7$—iso | $C_2H_5$ | $OC_2H_5$ | S | 77 | $n_D^{20}$:1.5380 |
| 4 | $C_4H_9$—tert. | H | $C_3H_7$—iso | $C_2H_5$ | $C_2H_5$ | S | 78 | $N_D^{20}$:1.5476 |
| 5 | $C_4H_9$—tert. | H | $C_2H_5$ | $CH_3$ | $OCH_3$ | S | 62 | $n_D^{20}$:1.5530 |

TABLE 2-continued

| Compound No. | R | $R^1$ | $R^2$ | $R^3$ | $R^4$ | X | Yield (% of theory) | Physical data (refractive index; melting point [°C.]) |
|---|---|---|---|---|---|---|---|---|
| 6 | $C_4H_9$—tert. | H | $C_2H_5$ | $C_2H_5$ | $CH_3$ | S | 72 | $n_D^{20}$:1.5587 |
| 7 | $C_4H_9$—tert. | H | $C_2H_5$ | $C_3H_7$—iso | $CH_3$ | S | 72 | 90–91 |
| 8 | $C_4H_9$—tert. | H | $C_2H_5$ | $C_2H_5$ | $C_2H_5$ | S | 60 | $n_D^{20}$:1.5528 |
| 9 | $C_4H_9$—tert. | H | $C_3H_7$—iso | $CH_3$ | $OCH_3$ | S | 59 | $n_D^{21}$:1.5478 |
| 10 | $C_4H_9$—tert. | H | $C_3H_7$—iso | $C_3H_7$—iso | $CH_3$ | S | 58 | 105 |
| 11 | $C_4H_9$—tert. | H | $C_3H_7$—iso | $C_2H_5$ | $CH_3$ | S | 65 | $n_D^{21}$:1.5526 |
| 12 | $C_4H_9$—tert. | H | $CH_3$ | $CH_3$ | $OCH_3$ | S | 27 | partially crystalline |
| 13 | $C_4H_9$—tert. | H | $CH_3$ | $CH_3$ | $OC_3H_7$—n | S | 54 | $n_D^{22}$:1.5470 |
| 14 | $C_4H_9$—tert. | H | $CH_3$ | $C_4H_9$—iso | $C_2H_5$ | S | 41 | $n_D^{22}$:1.5462 |
| 15 | $C_4H_9$—tert. | H | $C_2H_5$ | $C_2H_5$ | $OC_3H_7$—n | S | 82 | $n_D^{23}$:1.5401 |
| 16 | $C_4H_9$—tert. | H | $C_2H_5$ | $C_3H_7$—n | $OCH_3$ | S | 81 | $n_D^{23}$:1.5427 |
| 17 | $C_4H_9$—tert. | H | $C_2H_5$ | $C_2H_5$ | $OC_2H_5$ | O | 78 | $n_D$23:1.5231 |
| 18 | $C_4H_9$—tert. | H | $C_2H_5$ | $C_3H_7$—n | $C_2H_5$ | S | 85 | $n_D^{22}$:1.5478 |
| 19 | $C_4H_9$—tert. | H | $C_2H_5$ | $CH_3$ | $C_2H_5$ | S | 81 | $n_D^{22}$:1.5588 |
| 20 | $C_2H_5$ | $CH_3$ | $C_2H_5$ | $C_2H_5$ | $C_2H_5$ | S | 63 | $n_D^{25}$:1.5540 |
| 21 | $CH_3$ | H | $C_2H_5$ | $C_2H_5$ | $OC_2H_5$ | S | 91 | 70–75 |
| 22 | $CH_3$ | H | $C_2H_5$ | $C_2H_5$ | $C_2H_5$ | S | 99 | 102 |
| 23 | $CH_3$ | H | $C_2H_5$ | $C_2H_5$ | $SC_3H_7$—n | S | 95 | $n_D^{23}$:1.5585 |
| 24 | $CH_3$ | H | $C_2H_5$ | $C_2H_5$ | $OC_2H_5$ | O | 89 | 60–65 |
| 25 | $CH_3$ | H | $C_2H_5$ | $CH_3$ | $OCH_3$ | S | 77 | 105 |
| 26 | $C_3H_7$—iso | H | $C_3H_7$—iso | $C_2H_5$ | $C_2H_5$ | S | 75 | 50 |
| 27 | $C_3H_7$—iso | H | $C_3H_7$—iso | $C_2H_5$ | $OC_2H_5$ | S | 83 | 65 |
| 28 | $C_3H_7$—iso | H | $C_3H_7$—iso | $C_2H_5$ | $SC_3H_7$—n | S | 72 | $n_D^{28}$:1.5550 |
| 29 | $C_3H_7$—iso | H | $C_3H_7$—iso | $C_2H_5$ | $OC_2H_5$ | O | 68 | $n_D^{28}$:1.5155 |
| 30 | $C_3H_7$—iso | H | $C_3H_7$—iso | $CH_3$ | $OCH_3$ | S | 75 | 68 |
| 31 | $C_3H_7$—iso | H | $C_3H_7$—iso | $C_2H_5$ | $OC_3H_7$—n | S | 82 | $n_D^{28}$:1.5310 |
| 32 | $C_3H_7$—iso | H | $C_3H_7$—iso | $C_4H_9$—sec. | $CH_3$ | S | 80 | 80 |

The insecticidal and acaricidal activity of the compounds of this invention is illustrated by the following examples wherein the compounds according to the present invention are each identified by the number (given in brackets) from the preparative Example 1.

The known comparison compounds are identified as follows:

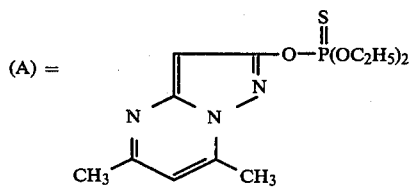

(A) =

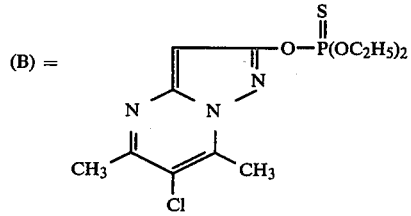

(B) =

EXAMPLE 2

Drosophila test

Solvent: 3 parts by weight of acetone.
Emulsifier: 1 part by weight of alkylaryl polyglycol ether.

To produce a suitable preparation of active compound, 1 parts by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

The active compounds, the concentrations of the active compounds, the evaluation times and the results can be seen from the following table:

TABLE 3

(Drosophila test)

| Active compound | Active compound concentration in % | Degree of destruction in % after 1 day |
|---|---|---|
| (A) | 0.1 | 0 |
| (B) | 0.1 | 0 |
| (12) | 0.1 | 100 |
| (25) | 0.1 | 100 |
| (21) | 0.1 | 100 |
| (24) | 0.1 | 100 |
| (22) | 0.1 | 100 |
| (23) | 0.1 | 100 |
| (20) | 0.1 | 100 |
| (1) | 0.1 | 100 |
| (8) | 0.1 | 100 |
| (6) | 0.1 | 100 |
| (19) | 0.1 | 100 |
| (16) | 0.1 | 100 |
| (7) | 0.1 | 100 |
| (18) | 0.1 | 100 |
| (9) | 0.1 | 100 |
| (4) | 0.1 | 100 |
| (30) | 0.1 | 100 |
| (27) | 0.1 | 100 |
| (29) | 0.1 | 100 |
| (26) | 0.1 | 100 |
| (28) | 0.1 | 100 |
| (31) | 0.1 | 100 |
| (32) | 0.1 | 100 |

EXAMPLE 3

Tetranychus test (resistant)

Solvent: 3 parts by weight of acetone.

Emulsifier: 1 part by weight of alkylaryl polyglycol ether.

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 4

| | (Tetranychus test/resistant) | |
|---|---|---|
| Active compound | Active compound concentration in % | Degree of destruction in % after 2 days |
| (A) | 0.1 | 0 |
| (B) | 0.1 | 0 |
| (25) | 0.1 | 70 |
| (24) | 0.1 | 100 |
| (15) | 0.1 | 80 |
| (11) | 0.1 | 70 |

EXAMPLE 4

Test with parasitic fly larvae

Solvent: 35 parts by weight of ethylene polyglycol monomethyl ether.

Emulsifier: 35 parts by weight of nonylphenol polyglycol ether.

To produce a suitable preparation of active compound, 30 parts by weight of the active substance in question were mixed with the stated amount of solvent which contained the above-mentioned porportion of emulsifier and the concentrate thus obtained was diluted with water to the desired concentration.

About 20 fly larvae (*Lucilia cuprina*) were introduced into a test tube which contained approx. 2 ml of horse muscle. 0.5 ml of the preparation of active compound was applied to this horse meat. After 24 hours, the degree of destruction in % was determined. 100% meant that all of the larvae had been killed and 0% meant that none of the larvae had been killed.

The active compounds, the concentrations of the active compounds and the results can be seen from the table which follows:

TABLE 5

| | (Test with parasitic fly larvae/ *Lucilia cuprina* res.) | |
|---|---|---|
| Active compound | Active compound concentration in ppm | Degree of destruction in % |
| (3) | 100 | 100 |
| | 30 | 100 |
| | 10 | 100 |
| (4) | 100 | 100 |
| | 30 | 100 |
| | 10 | 100 |
| (6) | 100 | 100 |
| | 30 | 100 |

TABLE 5-continued

| | (Test with parasitic fly larvae/ *Lucilia cuprina* res.) | |
|---|---|---|
| Active compound | Active compound concentration in ppm | Degree of destruction in % |
| | 10 | 100 |
| | 3 | 100 |
| | 1 | 100 |
| (9) | 100 | 100 |
| | 30 | 100 |
| | 10 | 100 |
| | 3 | 100 |
| (11) | 100 | 100 |
| | 30 | 100 |
| | 10 | 100 |
| | 3 | 100 |

EXAMPLE 5

Test on mange mites

Screening test on Psoroptes cuniculi/sandwich test in vitro

Solvent: 35 parts by weight of ethylene polyglycol monomethyl ether.

Emulsifier: 35 parts by weight of nonylphenol polyglycol ether.

To produce a suitable preparation of active compound, 30 parts by weight of the active substance in question were mixed with the stated amount of solvent which contained the above-mentioned proportion of emulsifier, and the concentrate thus obtained was diluted with water to the desired concentration.

Test acarids. Natural population (larvae, nymphs and adults) of the rabbit ear mite (*Psoroptes cuniculi*), which were collected one hour before the test, from the ears of infected rabbits.

Test procedure. 10–25 specimens per concentration were transferred into filterpaper sandwiches (diameter 7.5 cm) impregnated with active compound. The sandwiches were prepared by pipetting onto them 3 ml of the preparation, having the concentration to be tested. They were then transferred into, and stored in, a climatically controlled test chamber (28° C.±1° C., 80% relative humidity±10%). The effect was checked after 24 hours by means of a stereomicroscope, magnification 12.5 times).

Criterion. The criterion of the effect was the occurrence of death of the treated mites (signs of death=absence of voluntary limb movements after stimulation with a dissecting needle).

Rating

3=100% effect (all mites had been killed).

2=>50% effect (more than 50% of the mites had been killed).

1=<50% effect (fewer than 50% of the mites had been killed).

0=no effect (all mites were alive).

The active compounds, concentrations of active compounds and the results are shown in the following table.

TABLE 6

| | (Mange mite test/*Psoroptes cuniculi*) | |
|---|---|---|
| Active compound | Active compound concentration in ppm | Rating |
| (3) | 1,000 | 3 |
| | 300 | 3 |

TABLE 6-continued

| | (Mange mite test/*Psoroptes cuniculi*) | |
|---|---|---|
| Active compound | Active compound concentration in ppm | Rating |
| (4) | 100 | 3 |
| | 1,000 | 3 |
| | 300 | 3 |
| | 100 | 3 |
| | 30 | 3 |
| (6) | 1,000 | 3 |
| | 300 | 3 |
| | 100 | 3 |
| | 30 | 3 |
| | 10 | 3 |

It will be appreciated that the instant specification and examples are set forth by way of illustration and not limitation, and that various modifications and changes may be made without departing from the spirit and scope of the present invention.

What is claimed is:

1. O,O-diethyl-O-[5-carbethoxy-7-tert.-butyl-pyrazolo(1,5-α)-pyrimidin(2)yl]-thionophosphoric acid ester of the formula

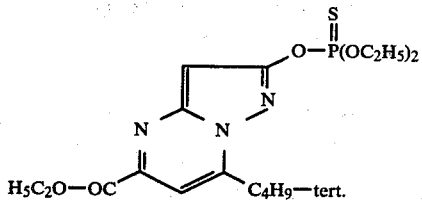

* * * * *

UNITED STATES PATENT AND TRADEMARK OFFICE
CERTIFICATE OF CORRECTION

PATENT NO. : 4,345,078
DATED : August 17, 1982
INVENTOR(S) : W. Hofer et al

It is certified that error appears in the above—identified patent and that said Letters Patent is hereby corrected as shown below:

| | |
|---|---|
| Col. 1, line 7 | Delete "relate" and insert --relates--. |
| Col. 1, line 57 | Second instance, delete "(phosphoric)" and insert --(phosphonic)-- |
| Col. 2, line 57 | Delete "material" and insert --materials-- |
| Col. 6, line 50 | Delete "Costelyra" and insert --Costelytra-- |
| Col. 9, line 42 | After "40g" delete "(0.1 mol)" and insert --(0.2 mol)--. |
| Col. 11, line 62 | Delete "parts" and insert --part--. |

Signed and Sealed this

Second Day of November 1982

[SEAL]

Attest:

Attesting Officer

GERALD J. MOSSINGHOFF

Commissioner of Patents and Trademarks